(12) United States Patent
de Josselin de Jong et al.

(10) Patent No.: US 7,813,790 B2
(45) Date of Patent: Oct. 12, 2010

(54) DENTAL IMPLEMENT AND METHOD FOR TOOTH SURFACE INSPECTION

(75) Inventors: Elbert de Josselin de Jong, Bussum (NL); Elbert Waller, Amsterdam (NL); Monique van der Veen, Almere (NL)

(73) Assignee: Inspektor Research Systems BV, Amsterdam (NL)

( * ) Notice: Subject to any disclaimer, the term of this patent is extended or adjusted under 35 U.S.C. 154(b) by 748 days.

(21) Appl. No.: 11/422,487

(22) Filed: Jun. 6, 2006

(65) Prior Publication Data

US 2006/0240377 A1  Oct. 26, 2006

Related U.S. Application Data

(63) Continuation of application No. 10/209,574, filed on Jul. 31, 2002.

(51) Int. Cl.
*A61B 6/00* (2006.01)
(52) U.S. Cl. .......... 600/476; 433/29; 433/215; 359/361; 607/88; 607/89; 607/100
(58) Field of Classification Search ........... 600/476; 433/29, 215; 359/361; 607/88, 89, 100
See application file for complete search history.

(56) References Cited

U.S. PATENT DOCUMENTS

| | | | |
|---|---|---|---|
| 3,711,700 A | | 1/1973 | Westlund, Jr. et al. |
| 4,266,535 A | | 5/1981 | Moret |
| 4,290,433 A | | 9/1981 | Alfano |
| 4,515,476 A | | 5/1985 | Ingmar |
| 4,900,253 A | | 2/1990 | Landis |
| 5,382,163 A | * | 1/1995 | Putnam ............ 433/215 |
| 5,894,620 A | | 4/1999 | Polaert et al. |
| 5,957,687 A | | 9/1999 | Brilliant |
| 6,024,562 A | * | 2/2000 | Hibst et al. ............ 433/29 |

(Continued)

FOREIGN PATENT DOCUMENTS

DE          3345465          6/1985

(Continued)

OTHER PUBLICATIONS

S. Albin et al.; Laser Induced Fluorescence of Dental Caries; Proceedings of the SPIE, Bellingham, VA, US; SPIE, 1988, pp. 96-98, vol. 907, XP000570174.

*Primary Examiner*—Brian Casler
*Assistant Examiner*—Baisakhi Roy
(74) *Attorney, Agent, or Firm*—Matthew R. Schantz; Bingham McHale LLP (57) ABSTRACT

Described are dental implements useful for inspecting tooth surfaces for abnormalities such as caries or plaque. Preferred implements of the invention include light-emitting diodes mounted on an implement body having a mirror for insertion into a user's mouth. Such implements also have on-board batteries mounted in chambers in the implement handle, and a switch for energizing and de-energizing the LED with the battery. Also described are methods for examining tooth surfaces for abnormal conditions indicative of plaque involving illuminating surfaces with radiation at a wavelength in the range of 390-450 nm wherein the radiation is effective to cause detectable fluorescence emissions from bacterial metabolites known to be associated with plaque-containing surfaces, and detecting the emissions.

26 Claims, 7 Drawing Sheets

U.S. PATENT DOCUMENTS

| | | |
|---|---|---|
| 6,231,338 B1 | 5/2001 | de Josselin de Jong |
| 6,325,623 B1 * | 12/2001 | Melnyk et al. ............... 433/29 |
| 6,485,300 B1 * | 11/2002 | Muller et al. ............... 433/29 |
| 2003/0022126 A1 | 1/2003 | Buchalla et al. |
| 2003/0156788 A1 * | 8/2003 | Henning ............... 385/31 |
| 2004/0023184 A1 * | 2/2004 | de Josselin de Jong et al. .. 433/30 |
| 2005/0080465 A1 * | 4/2005 | Zelickson et al. ............. 607/88 |

FOREIGN PATENT DOCUMENTS

| | | |
|---|---|---|
| DE | 4032779 | 4/1992 |
| DE | 20209441 | 9/2002 |
| GB | 2256938 | 12/1992 |
| GB | 2340618 | 2/2000 |
| WO | 9012541 | 11/1990 |
| WO | 9959462 A | 11/1999 |

* cited by examiner

DENTAL IMPLEMENT AND METHOD FOR TOOTH SURFACE INSPECTION

FIELD OF THE INVENTION

The present invention relates generally to devices and methods for inspecting tooth surfaces, and in particular to such devices and methods involving the detection of differential fluorescence emissions from abnormal and healthy tooth surfaces.

BACKGROUND

Various devices and methods have been proposed that involve using fluorescence emissions to detect caries or other abnormal conditions. For example, U.S. Pat. No. 3,711,700 relates to a disclosing light for inspecting tooth surfaces. The disclosing light is designed for use in conjunction with a fluorescent dye such as sodium fluorescein. The disclosing light includes a light source and a dichroic reflector behind the light source to reflect blue light forward and the remainder backward. A second dichroic filter is positioned in front of the light source and transmits blue light and reflects back infrared radiation. A mirror reflects yellow light to the observer and transmits other wavelengths.

U.S. Pat. No. 4,266,535 discloses a diagnostic lamp for use in conjunction with a fluorescent dye to inspect tooth surfaces. The lamp includes an incandescent bulb light source used in conjunction with a lens to supply a divergent beam of rays. A blue filter with an applied dichroic filter is used to filter the rays, which are made to impinge upon the fluorescent dye. The resulting fluorescence can be viewed in a folding, adjustable mirror. U.S. Pat. No. 5,957,687 discloses another diagnostic unit including a filtered light source and a mirror contained in a housing. Filtered light is concentrated in the blue frequency range and causes fluorescent dye to fluoresce. This can then be viewed in the mirror.

U.S. Pat. No. 4,290,433 discloses a method and device for detecting caries in human teeth using luminescence. The luminescence from teeth is measured at two predetermined wavelengths, one of which is about the same for caries-containing and non-caries-containing surfaces, and another where the luminescence is higher for caries-containing surfaces. A signal is generated corresponding to the difference in the intensities at the two measured wavelengths. A baseline measurement is taken at a non-decayed region, and the probe is then directed to other regions to assess the presence or absence of caries.

U.S. Pat. No. 4,515,476 describes a device for the ocular determination of discrepancies in the luminescence capacity of tooth surfaces. The disclosed device includes an argon laser for generating visible light in a predetermined wavelength range that causes luminescence from tooth surfaces. An absorption filter is used to eliminate reflections and luminescence within the predetermined wavelength range of the laser light. In this fashion, unsound tooth surface areas such as caries can be viewed as dark areas.

U.S. Pat. No. 5,894,620 discloses an electric toothbrush with means for locating dental plaque. The electric toothbrush includes an optical fiber for transmitting excitation radiation to tooth surfaces, and an optical fiber(s) for receiving a return luminescence or fluorescence signal. The return signal is then processed to activate a light or audible signal indicative of the presence of plaque.

In light of this background, there remain needs for improved, convenient devices and methods for tooth surface inspection to detect caries and other surface abnormalities. The present invention is addressed to these needs.

SUMMARY

Accordingly, in one embodiment, the invention provides a hand-held dental implement for use in detecting abnormal tooth surface conditions. The dental implement includes an implement body having a proximal handle connected to a distal end, and a mirror mounted on the distal end and adapted for insertion into the mouth of the user. The proximal handle defines a battery chamber for receiving a battery. The battery chamber has a positive electrical connection and a negative electrical connection for electrical contact with respective positive and negative terminals of the battery. At least one light-emitting diode is mounted on the implement and has positive and negative leads electrically connected to the positive electrical connection and said negative electrical connection, respectively, so as to be energizable by the battery. The light-emitting diode is effectively positioned on the implement to illuminate tooth surfaces of the user when the mirror is positioned in the mouth of the user, and is effective to emit radiation that causes visually detectable differential fluorescence emissions from normal tooth surfaces and abnormal tooth surfaces. A switch is provided on the implement and has a first condition wherein the light-emitting diode is energized by the battery, and a second condition wherein the light-emitting diode is not energized by the battery. In one embodiment, the light-emitting diode is adapted to emit light having a peak intensity in the wavelength range of about 390 nm to about 500 nm. In another embodiment, the implement includes a light filter positioned to filter the differential fluorescence emissions for direct visualization by the user.

Another embodiment of the invention provides a hand-held dental implement for detecting abnormal tooth surface conditions. The dental implement includes a handle having a proximal end and distal end. A battery chamber is present in the handle for receiving a battery. A light source is mounted on the implement and is electrically connected to the battery chamber, wherein the light source is energizable by a battery received in the battery chamber. The light source is adapted for insertion into the mouth of a user and effective to illuminate tooth surfaces sufficiently to cause visually detectable differential fluorescence emissions from normal tooth surfaces and abnormal tooth surfaces. A filter is included with the implement and is positioned to filter the fluorescence emissions for direct visualization by the user. The light source is desirably adapted to emit light having a peak intensity in the wavelength range of about 390 to about 500 nm, and in one embodiment in the peak intensity is in the wavelength range of 390 nm to about 450 nm. In this lower wavelength range, fluorescence emissions can be directly visualized to detect both carious surfaces (yellow-green emissions) and surfaces containing or covered with bacterial metabolites associated with plaque (red-orange emissions).

Another embodiment of the invention provides a method for examining tooth surfaces for abnormal surface conditions. The method includes illuminating the tooth surfaces with light from a light-emitting diode having a peak intensity in the wavelength range of about 390 nm to about 500 nm, wherein the illuminating is effective to cause visually detectable differential fluorescence emissions from normal tooth surfaces and abnormal tooth surfaces. Fluorescence emissions from the normal and abnormal tooth surfaces are filtered and the differential fluorescence emissions are visually detected.

In another embodiment, the invention provides an apparatus for examining tooth surfaces for abnormal surface conditions. The apparatus includes a light-emitting diode adapted when energized to emit radiation having a peak intensity in a wavelength range from 390 to 500 nm, wherein the emitted radiation is effective to cause detectable differential fluorescence emissions from normal tooth surfaces and abnormal tooth surfaces. Means for energizing the diode are provided, along with at least one filter for filtering the fluorescence emissions to facilitate detection of the differential fluorescence emissions.

A still further embodiment of the invention provides a method for detecting plaque-containing surfaces in the oral cavity (including areas such as tooth surfaces, gums, in interproximal areas, in tooth fissures, or in caries lesions). The method includes illuminating areas of the oral cavity with radiation having a peak intensity at a wavelength in the range of 390 to 450 nm, wherein the radiation is effective to cause detectable fluorescence emissions from bacterial metabolites known to be contained within plaque. The fluorescence emissions are then detected.

The present invention provides improved and alternative implements, apparatuses and methods for inspecting tooth surfaces for abnormalities such as caries or bacterial metabolites potentially indicative of plaque. Additional embodiments as well as features and advantages of the invention will be apparent to those of ordinary skill in the art from the descriptions herein.

DESCRIPTION

For the purposes of promoting an understanding of the principles of the invention, reference will now be made to certain embodiments thereof and specific language will be used to describe the same. It will nevertheless be understood that no limitation of the scope of the invention is thereby intended. Any alterations and further modifications in the described embodiment, and any further applications of the principles of the invention as illustrated herein being contemplated as would normally occur to one skilled in the art to which the invention relates are also included.

As disclosed above, one embodiment of the present invention provides a hand-held dental implement for use in detecting abnormal tooth surface conditions. Generally, such dental implements of the invention incorporate components enabling the use of Quantitative Light-induced Fluorescence or "QLF" to provide direct visualization of areas having incipient caries lesions, plaque, stains or other abnormal tooth surface conditions or deposits. Such devices can be used to conduct self-examinations or examinations of others in household or clinical settings.

Figure 1:
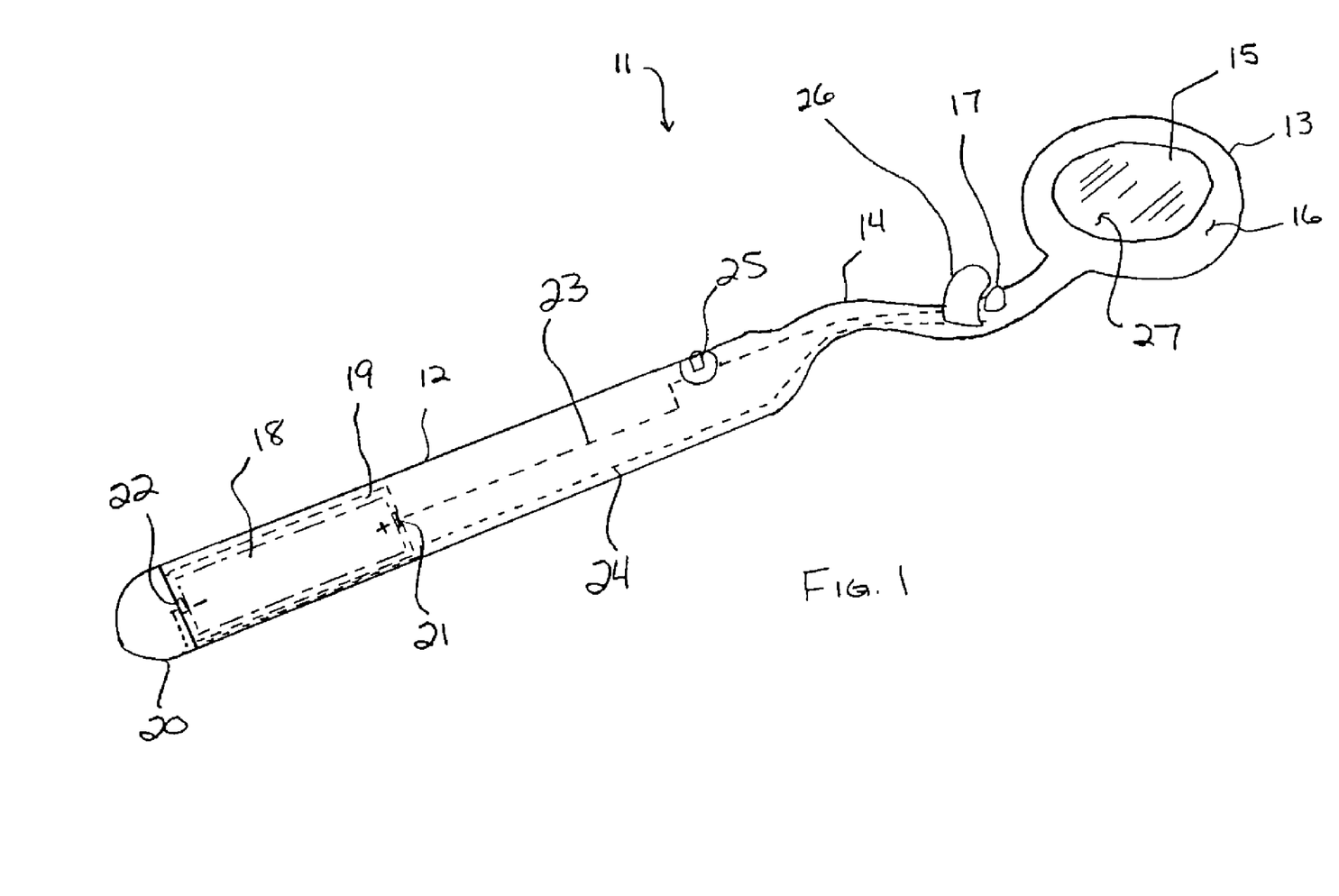
FIG. 1 provides a perspective view of one embodiment of an inventive dental implement for inspection of tooth surfaces.

Referring now to FIG. 1, an illustrative dental implement of the invention is shown. In particular, shown is a dental implement 11 useful for inspecting tooth surfaces to detect abnormal conditions. Dental implement 11 generally includes an implement body having a handle portion 12 connected to a mirror portion 13 through a transitional portion 14. Transitional portion 14 may be contoured to position the mirror portion 13, and in particular the face of mirror 15, at an angle relative to the axis of handle portion 12, so as to facilitate proper positioning of mirror 15 for viewing tooth surfaces. Mirror 15 may be circular or oval as shown or may have any other suitable shape for insertion into the mouth of a user. Mirror portion 13 includes a mirror housing 16 surrounding and mounting the mirror 15. Dental implement 11 also includes a blue light source 17 mounted on the implement 11, and in the illustrative embodiment mounted within the transitional portion 14 of the implement body. Blue light source 17 is preferably adapted to emit light having a peak intensity in the wavelength range of about 390 nm to about 500 nm, more desirably in the wavelength of about 390 nm to about 450 nm. Blue light source 17 advantageously includes a light-emitting diode having the described characteristics. The light-emitting diode may or may not have a collimator optical system integrated therein. Suitable light-emitting diodes for these purposes are commercially available from Cree, Inc., under product codes C405-XB900-x and C405-MB290-E400. Blue light-emitting diodes having a peak wavelength of about 405 nm have been particularly advantageous in work to date.

Dental implement 11 also includes an on-board battery 18 mounted within a housing 19 defined by the implement body 11, and in the illustrated device defined within the handle portion 12 of the implement body 11. Access to the housing 19 may be provided, for example, by a cap 20 threadable onto the end of handle portion 12 of the implement body. Other access means may also be provided. Battery housing 19 includes a positive battery contact 21 and a negative battery contact 22 for contacting positive and negative terminals of battery 18, respectively. Positive contact 21 is electrically connected to positive wire 23 and negative contact 22 is connected to negative wire 24. Wires 23 and 24 and other components of the electrical system are preferably housed within the implement body 11. Positive wire 23 is connected to a positive lead of the light-emitting diode 17 or other light source and negative wire 24 is connected to a negative lead of the light-emitting diode 17 or other light source. The battery 18 may be replaceable or may be rechargeable. In the latter case, the implement 11 may be provided and electrically matable with a recharging stand or other recharging instrument adapted to be plugged into an electrical outlet in a home or office. Likewise, in another inventive embodiment, a dental implement similar to implement 11 could itself be adapted to be plugged into and powered from such an electrical outlet.

A switch 25 for energizing and de-energizing the light source 17 with the battery is provided. Switch 25 may be any suitable switch for these purposes including vertically-displaceable push-button switches, or horizontally-displaceable slide switches. Further, other switching mechanisms may be built into the device including for example inertial switches optionally in combination with appropriate circuitry for energizing the light source 17 for a predetermined period of time upon actuation of the inertial switch. These and other switches will be recognized as useful in the present invention by those of ordinary skill in the art.

Dental implement 11 also includes an opaque or other suitable shield 26 for shielding blue light emitted by blue light source 17 and preventing such blue light from direct visualization by a user of dental implement 11, which could possibly corrupt visualization of the desired fluorescence signal. To this end, shield 26 will be mounted proximal to the blue light source 17 to prevent direct visualization of the emitted blue light by a user of the implement 11.

Dental implement 11 also includes a light filter 27 for filtering light. For use in the invention, filter 27 may, for example, filter light based upon wavelength or based upon polarization. When a wavelength-based filter is used, it is preferable that the light source 17 emit no significant amount of light above the cut-off wavelength of the filter. For example, when using a blue light source with an intensity peak in the wavelength range of 390 nm to 450 nm, it is desirable to use a yellow filter with a cutoff of about 520 nm. When using polarization as a means for the filter, the optical filter desirably will eliminate all polarized light originating from the illuminated area as the fluorescence signal will be randomly polarized. In the illustrated embodiment, light filter 27 is coated or layered onto the surface of the mirror 15.

In use of the dental implement 11, when the mirror portion 13 is inserted into the mouth of a user with the mirror 15 positioned to view tooth surfaces, and blue light source 17 is energized, tooth surfaces will be impinged by the blue light from the blue light source 17 and caused to fluoresce in the green wavelength range. Such green fluorescence from healthy and unhealthy tooth surfaces will pass through the yellow filter 27 prior to visualization by the user. Potentially corruptive light from the blue light source 17 and fluorescence at wavelengths below the cut-off for the yellow filter 27 will not pass through the filter 27. Because fluorescence from carious tooth surfaces in the green spectrum is less intense than that from healthy tooth surfaces, carious tooth surfaces will appear as dark areas or patches visible to the user of the dental implement 11.

Figure 2:
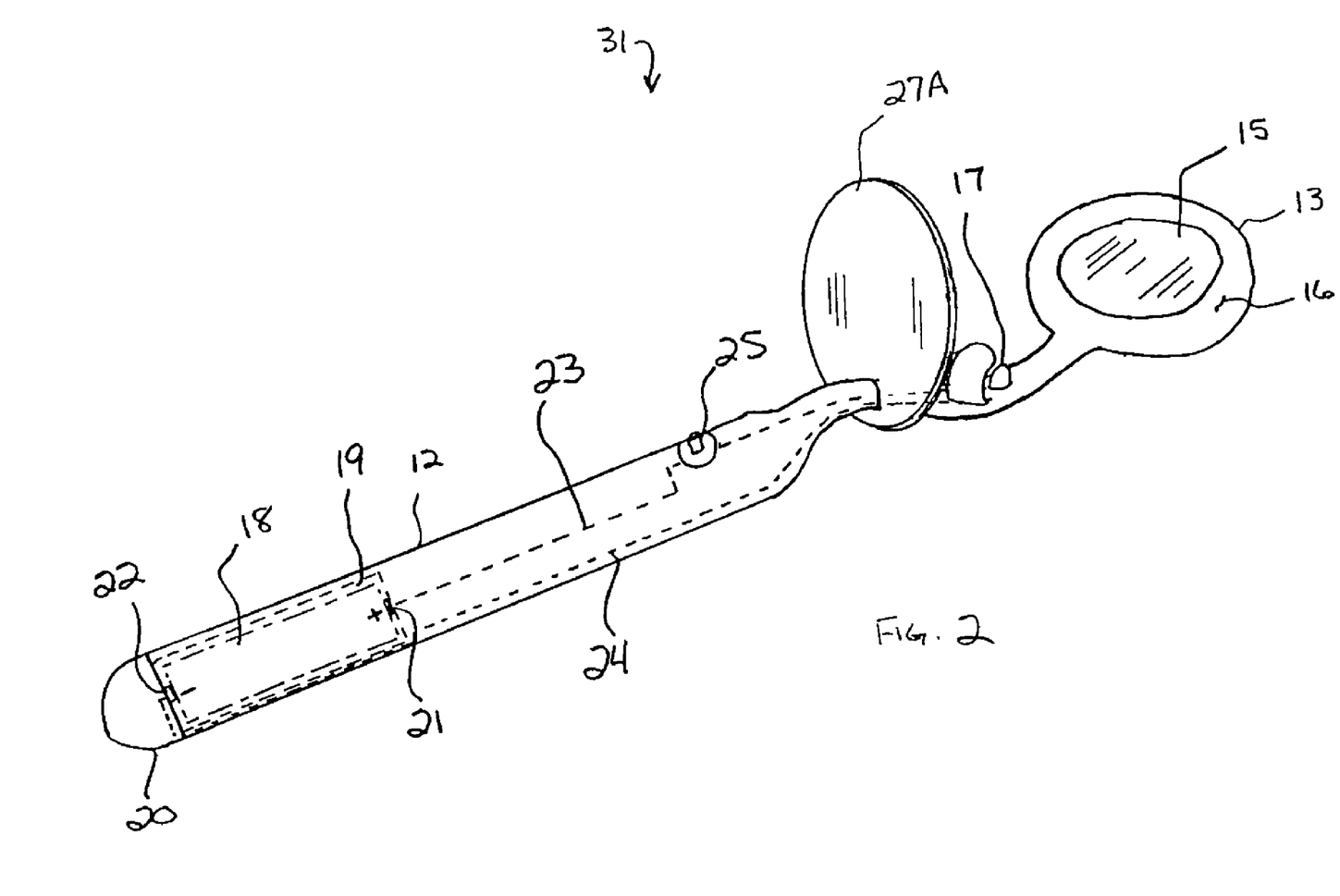
FIG. 2 provides a perspective view of an alternative embodiment of a dental implement for tooth inspection having a yellow filter mounted on the implement body.

With reference now to FIG. 2, shown is another dental implement 31 in accordance with the present invention. Dental implement 31 has similar components to dental implement 11 (FIG. 1), except implement 31 has no yellow filter coated onto mirror 15, but rather has a yellow filter 24A mounted on the implement body and in particular on the transitional portion 14 thereof. In this fashion, again, potentially corruptive reflected light and fluorescence emissions will not pass through filter 24A, whereas fluorescence emissions in the green spectrum will pass and be visualized by a user of implement 31 revealing caries lesions as dark areas. Yellow filter 24A can be of circular or oval shape as shown, or of any other suitable shape. Filter 24A is generally sized and positioned to enable visualization of light reflecting from mirror 15 and through filter 24A.

Figure 3:
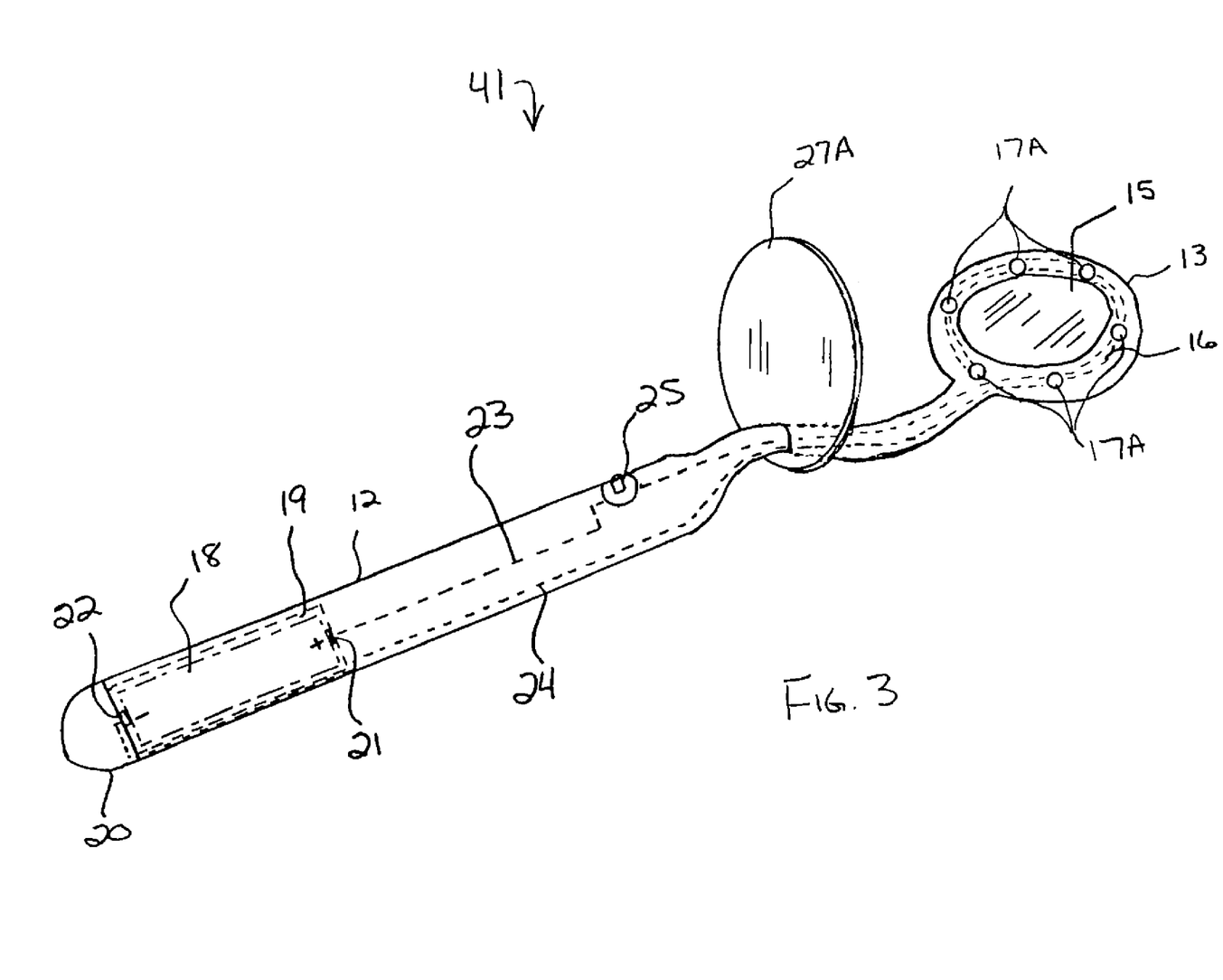
FIG. 3 provides a perspective view of an alternative embodiment of a dental implement for tooth inspection having light sources mounted in a mirror housing.

With reference now to FIG. 3, shown is another dental implement 41 having an alternative light source configuration. Implement 41 has features similar to those of implement 31 (FIG. 2), except implement 41 has multiple light sources 17A housed within the mirror portion 13 and in particular housed circumferentially within the mirror housing 16 surrounding the mirror 15. Light sources 17 may, for example, be a plurality of blue LEDs as described hereinabove.

Figure 4:
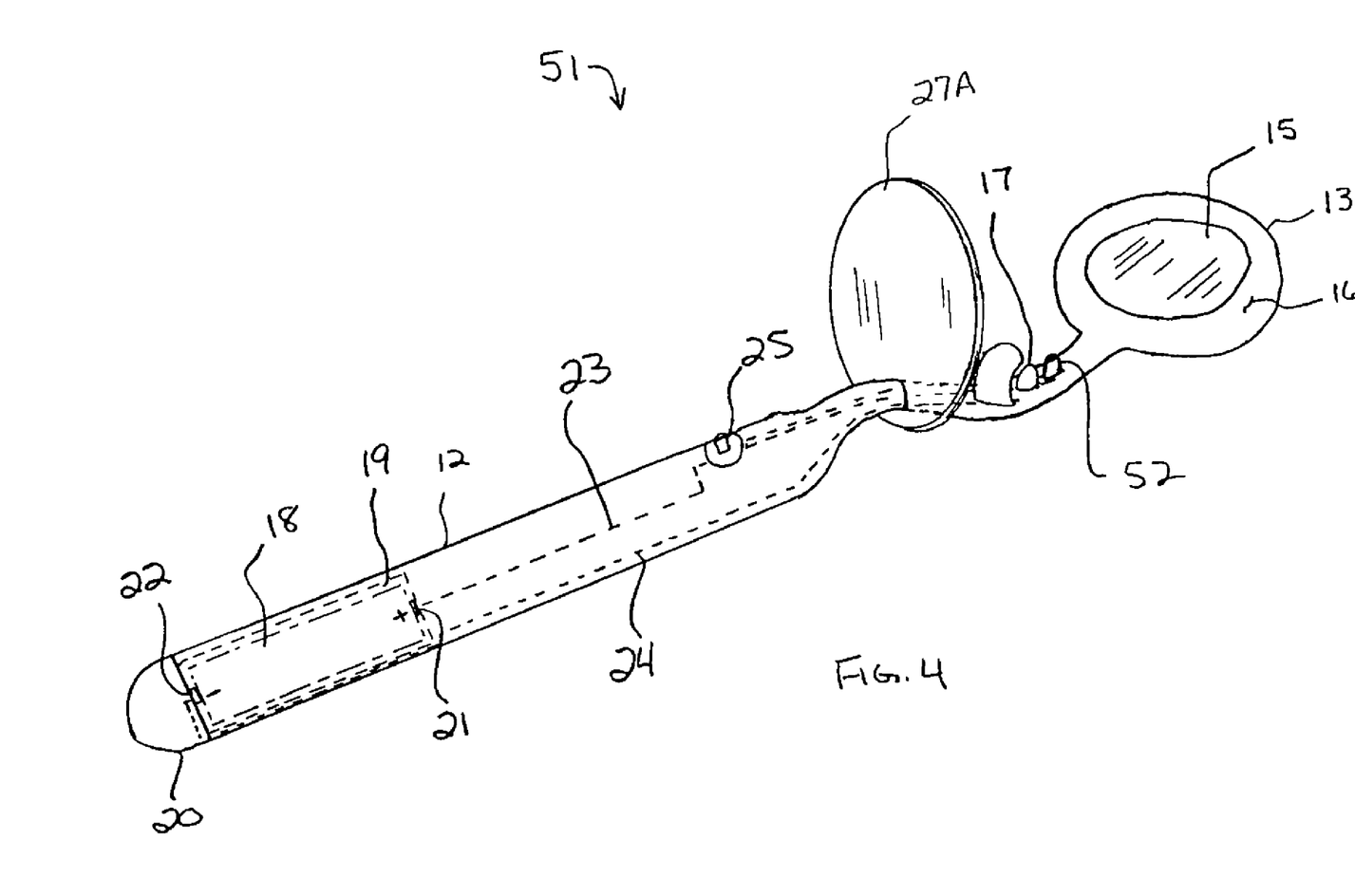
FIG. 4 is a perspective view of an alternative embodiment of a dental implement having both blue and white light sources mounted on the implement body.

Referring now to FIG. 4, shown is an alternative dental implement 51 of the invention having features similar to those of dental implement 31 (FIG. 2), except having a white light source 52 in addition to the blue light source 17. In dental implement 51, the switch 25 is a three-position switch for selectively energizing the blue light source 17, the white light source 52, or de-energizing both light sources 17 and 52. Dental implement 51 thus enables a selection by the user between fluorescence-based visualization and normal reflected white-light visualization. This assists the user in differentiating among caries-containing tooth surfaces and stained tooth surfaces, both of which can appear as dark areas in the fluorescence-based visualization.

Figure 5:
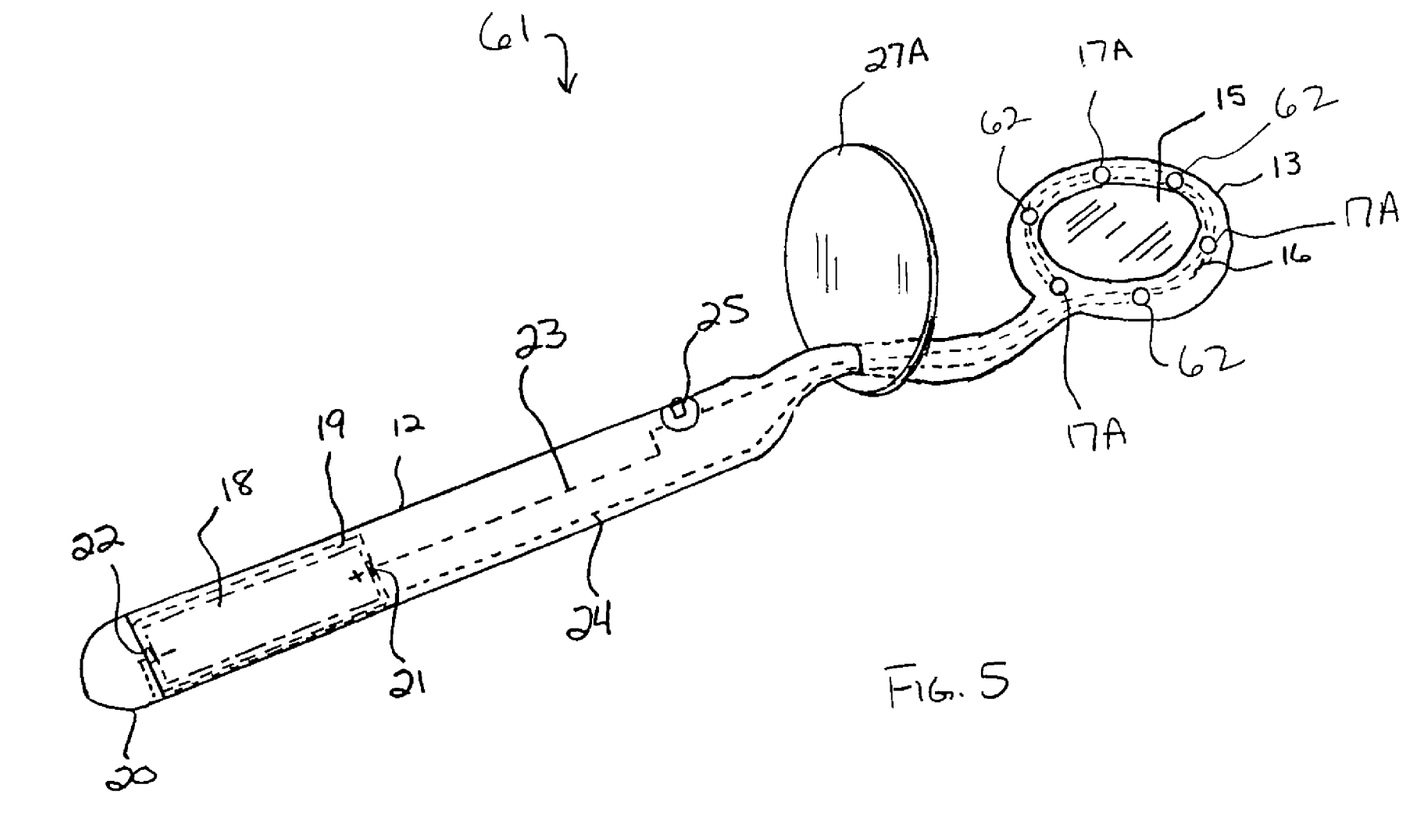
FIG. 5 provides a perspective view of an alternative embodiment of a dental implement having blue and white light sources mounted in a mirror housing.

FIG. 5 shows another dental implement 61 according to the present invention. Dental implement 61 includes both blue light sources 17A and white light sources 62 similar to prior-discussed implement 51 (FIG. 4), except having the light sources mounted in the mirror housing 16 in a fashion similar to implement 41 (FIG. 3). Switch 25 in dental implement 61 thus is a three-position switch for selectively energizing the plurality of white light sources 62, the plurality of blue light sources 17A, or for de-energizing all light sources.

Figure 6:
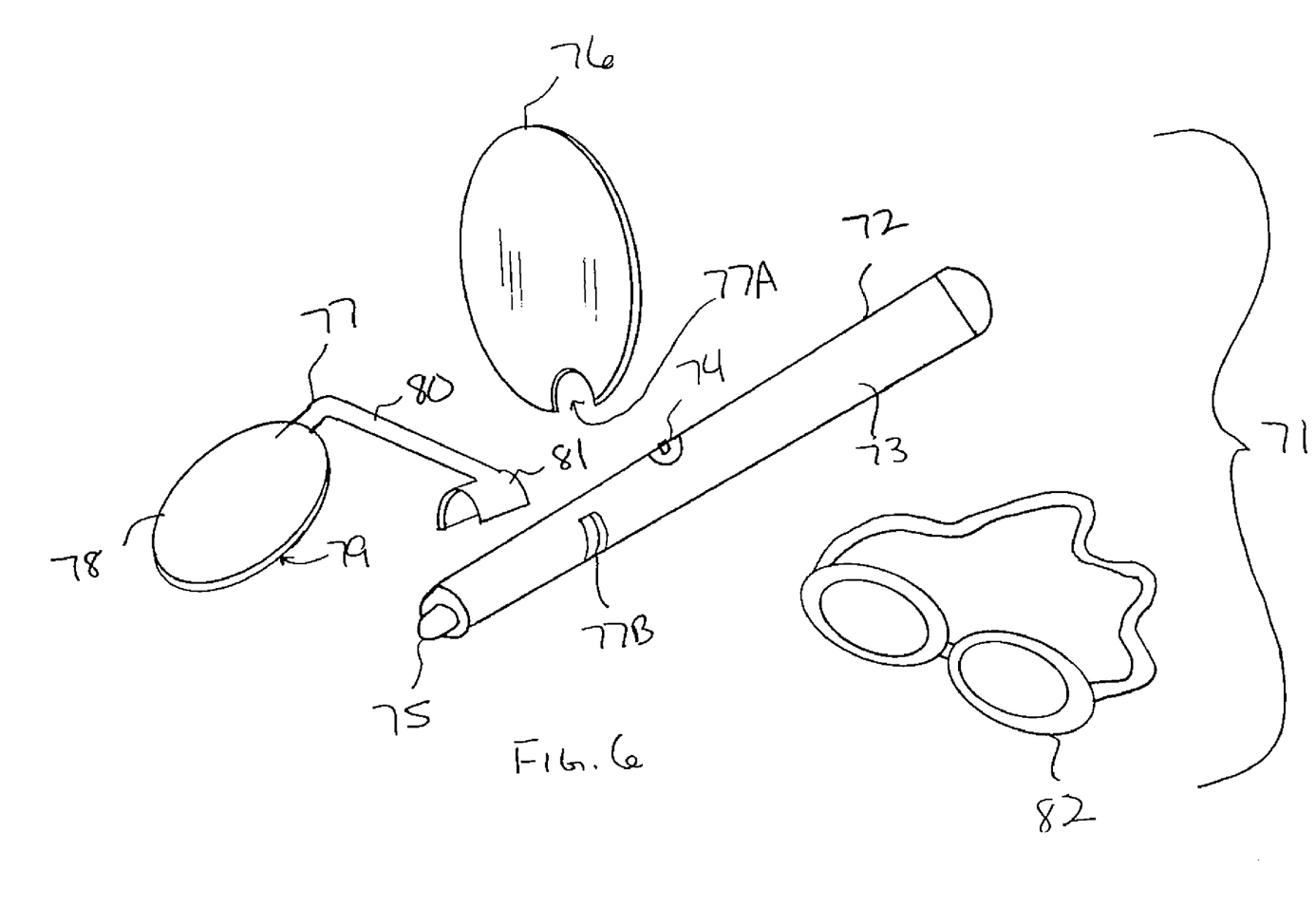
FIG. 6 provides a perspective view of an alternative embodiment of a dental implement having detachable filter and mirror components.

Referring now to FIG. 6, disclosed is another dental implement 71 according to the present invention. Implement 71 includes a body 72 including a handle portion 73 defining a battery chamber for receiving a battery similar to the corresponding components in implement 11 (FIG. 1). Implement body 72 includes a switch 74 for selectively energizing and de-energizing a blue light source 75 with a battery housed in the housing. Implement 71 also includes a yellow filter 76 that is detachable from the implement body 72, for example, having a cut-out portion 77A adapted to mate with a groove 77B in implement body 72 to achieve a friction or snap fit of the filter 76 to the implement body 72. Implement 71 also includes a detachable mirror unit 78 having a mirror 79, a stem 80 portion, and an attachment portion 81 adapted for friction or snap fit with the implement body 72. Such separate components may be sold together in a kit for assembling the dental implement. In addition to, or as an alternative to, attachable filter 76, dental implement 71 or kits for the same may include glasses 82 or other devices adapted to be worn over the eyes, containing a yellow filter(s) for filtering fluorescence to be viewed. In implement 71, blue light source 75 is advantageously located at or near the tip of the implement body 72 for effective illumination of tooth surfaces with the blue light source 75 (e.g., LED). As well, the detachable mirror unit 78 may be attached to the implement body 72 at varying positions thereby providing flexibility in the configuration of the mirror 79 relative to the handle portion 73, so as to enable user optimization of tooth visualization.

Figure 7:
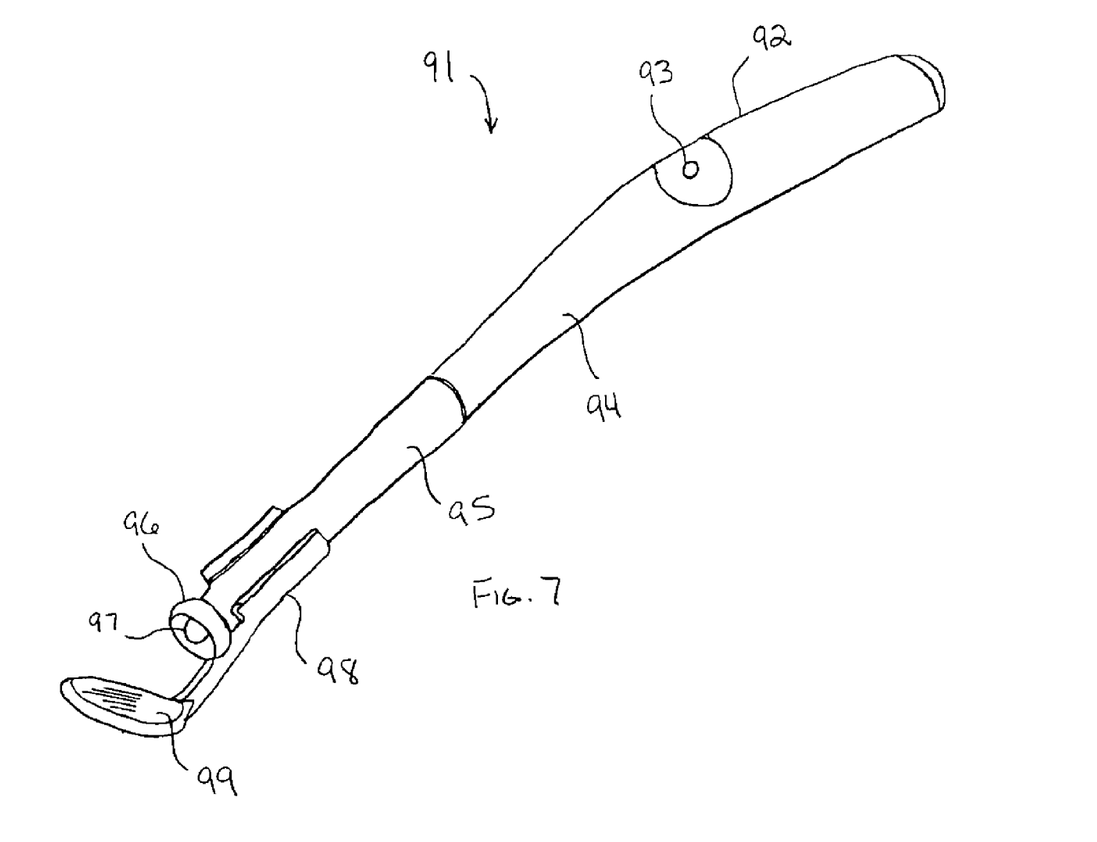
FIG. 7 provides a perspective view of another dental implement of the invention having a detachable mirror component.

With reference now to FIG. 7, shown is another alternative dental implement 91 of the invention. Dental implement 91 includes an implement body 92 having a switch 93 for energizing and de-energizing a light-emitting diode 97 with a battery (not shown) located within the implement body 92. Implement body 92 includes a generally curved handle portion 94 connected to a transitional portion 95 which may be integral with handle portion 94, or as shown may be a separate piece 95 connected to handle portion 94. Transitional portion 95 terminates in a generally cone-shaped terminus 96 defining a concave inner surface, optionally made of or coated with a reflective material, and within which is located a blue light emitting diode 97. Light-emitting diode 97 may be any one of those identified above. Dental implement 91 further includes a mirror unit 98 connectable to implement body 92 by a snap or friction fit. Mirror piece 98 further includes a mirror surface 99. Mirror unit 98 is adapted so that when attached to implement body 92, light emitted by the diode 97 reflects from the mirror surface 99 and on to the oral cavity (e.g. tooth) surfaces to be viewed. The fluorescence signals from the surface are then reflected back onto and from mirror surface 99 for visualization by a user (the mirror unit 78 and implement body 72 of implement 71, FIG. 6, can be adapted to similarly direct the paths of the light source and fluorescence signals). Implement 91 can be used in conjunction with a yellow filter positioned to filter the fluorescence signals reflected from mirror surface 99 prior to viewing. The yellow filter can be in the form of goggles (e.g. item 82, FIG. 6), a separate filter portion mounted on implement body 92 (e.g. such as item 76, FIG. 6), a filter adapted to be mounted on another mirror surface in the proximity of the user (e.g. a bathroom mirror), or the like.

Additional aspects of the present invention relate to the discovery that when more energetic (shorter wavelength) blue light is utilized, metabolic products of bacteria that typically reside in plaque, tarter, gingiva (pockets), dental tissue (lesions, cavities, cracks) and unpolished restorative materials (leaks around fillings, unpolished restorative surfaces, and cracks in restorative materials), will be cause to emit visually detectable red to orange fluorescence (about 500 to about 700 nm). In particular aspects, orange to red fluorescence (in the range of about 590 to about 700 nm) is emitted by porphyrin materials that are produced primarily by anaerobic bacteria linked to gingivitis and extracellular or intracellular polysaccharides (linked to consumption of sugars such as glucose and saccharose). Preferred excitation radiation for these purposes falls within the wavelength range of about 390 nm to about 450 nm. In certain embodiments of the invention, the detection of the red to orange fluorescence is be used in conjunction with the dental implements, apparatuses and methods described above. Detection of the red to orange fluorescence can also be used in other systems for monitoring dental tissue. For example, the condition of dental tissue and deposits over time can be monitored by capturing periodic images showing areas of the orange to red fluorescence. These images can be reviewed and displayed to patients alone or in conjunction with fluorescence-based images of carious regions, in slideshow or animated formats. In one mode of operation, tooth fluorescence emissions obtained with a blue excitation source can be digitally acquired and digitally filtered using an appropriate digital processor to separate the yellow-green (carious detection range) and red-orange (bacterial metabolite detection range) fluorescence images. The original and separated fluorescence images can then be displayed concurrently on an interface to facilitate advising patients of their dental health and of the results of their dental hygiene regimen.

It will be understood that in inventive dental implements such as those depicted in FIGS. 1-7, the light-emitting diode or diodes can be mounted in an alternate location, such as within the handle, and an optical fiber or other suitable light guide can be used to transmit the light to an appropriate location external of the implement for illumination of the oral cavity, for example, a location consistent with the positions of the light-emitting diodes shown in FIGS. 1-7. These and other similar adaptations of the light source will be apparent to those of ordinary skill in the art from the descriptions herein.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety as if each had been individually incorporated by reference and fully set forth.

What is claimed is:

1. A hand-held dental implement for use in detecting abnormal tooth surface conditions, comprising:

an implement body having a proximal handle connected to a distal end;

a mirror mounted on said distal end, said mirror adapted for insertion into the mouth of the user;

a battery chamber in said proximal handle;

a positive electrical contact in said battery chamber, and a negative electrical contact in said battery chamber, for electrical contact with respective positive and negative terminals of a battery received in said battery chamber;

a light-emitting diode mounted on said implement, said light-emitting diode having positive and negative leads electrically connected to said positive electrical connection and said negative electrical connection, respectively, said light-emitting diode energizable by a battery received in said battery chamber;

said light-emitting diode effectively positioned on said implement to illuminate tooth surfaces of the user when said mirror is positioned in the mouth of the user;

said light-emitting diode effective to emit radiation having a peak intensity in the wavelength rage of about 390 nm to about 450 nm that causes visually detectable differential yellow-green and red-orange fluorescence emissions from normal tooth surfaces and abnormal tooth surfaces, respectively;

a filter external of said handle and positioned to filter said differential fluorescence emissions for direct visualization by the user, said filter being a cut-off filter that does not pass the wavelength below the cut-off wavelength, about 520 nm, and a switch on said implement, said switch having a first condition wherein said light-emitting diode is energized by said battery, and a second condition wherein said light-emitting diode is not energized by said battery.

2. The hand-held dental implement of claim 1, wherein said light-emitting diode effective to emit radiation having a peak intensity in the wavelength of about 405 nm.

3. The hand-held dental implement of claim 1, further comprising: a shield adjacent said light-emitting diode and configured to shield light emitted by said diode from direct visualization by a user.

4. The hand-held dental implement of claim 1, wherein said light source is positioned on said implement body.

5. The hand-held dental implement of claim 1, wherein said mirror is within a mirror housing, and wherein said light source is positioned within said mirror housing.

6. A hand-held dental implement for detecting abnormal tooth surface conditions, comprising:

a handle having a proximal end and distal end;

a battery chamber in said handle, for receiving a battery;

a light-emitting diode mounted on said device, said light-emitting diode electrically connected to said battery chamber, said light-emitting diode energizable by a battery received in said battery chamber;

said light-emitting diode insertable into the mouth of a user and effective to emit a light having a peak intensity in the wavelength range of about 390 nm to about 450 nm to tooth surfaces sufficiently to cause visually detectable differential yellow-green and red-orange fluorescence emissions from normal tooth surfaces and abnormal tooth surfaces, respectively; and a filter external of said handle and positioned to filter said fluorescence emissions for direct visualization by a user, said filter being a cut-off filter that does not pass the wavelength below the cut-off wavelength, about 520 nm.

7. The hand-held dental implement of claim 6, wherein said light-emitting diode effective to emit radiation having a peak intensity in the wavelength of about 405 nm.

8. The hand-held dental implement of claim 6, also including a mirror adapted for insertion into the mouth of the user.

9. The hand-held dental implement of claim 6, also including a white light source mounted on said implement.

10. An apparatus for examining tooth surfaces for abnormal surface conditions, comprising:
a light-emitting diode adapted when energized to emit light in a wavelength range from 390 nm to 450 nm, said light effective to cause visually detectable differential yellow-green and red-orange fluorescence emissions from normal tooth surfaces and abnormal tooth surfaces, respectively;
means for energizing said light-emitting diode;
at least one filter for filtering said fluorescence emissions to facilitate detection of said differential fluorescence emissions, said filter being a cut-off filter that does not pass the wavelength below the cut-off wavelength, about 520 nm.

11. The apparatus of claim 10, wherein said light-emitting diode effective to emit radiation having a peak intensity in the wavelength of about 405 nm.

12. The apparatus of claim 10, also comprising: a hand-held dental implement body;
wherein said light-emitting diode is attached to said body; and
wherein said means for energizing includes a battery mounted on said body.

13. The apparatus of claim 10, wherein said at least one filter is mounted on said body.

14. A dental implement for use in detecting abnormal tooth surface conditions, comprising:
an implement body having a proximal handle connected to a distal end;
a mirror mounted on said distal end, said mirror adapted for insertion into the mouth of the user;
a battery chamber in said proximal handle;
a positive electrical contact in said battery chamber, and a negative electrical contact in said battery chamber, for electrical contact with respective positive and negative terminals of a battery received in said battery chamber;
a light-emitting diode mounted on said implement, said light-emitting diode having positive and negative leads electrically connected to said positive electrical connection and said negative electrical connection, respectively, said light-emitting diode energizable by a battery received in said battery chamber;
said light-emitting diode effectively positioned on said implement to illuminate tooth surfaces of the user when said mirror is positioned in the mouth of the user;
said light-emitting diode effective to emit radiation having a peak intensity in the wavelength range of about 390 nm to about 450 nm that causes visually detectable differential yellow-green and red-orange fluorescence emissions from normal tooth surfaces and abnormal tooth surfaces, respectively;
a filter external of said handle and positioned to filter said differential fluorescence emissions for direct visualization by the user of fluorescence in the green-yellow wavelength range and orange-red wavelength range, and
a switch on said implement, said switch having a first condition wherein said light-emitting diode is energized by said battery, and a second condition wherein said light-emitting diode is not energized by said battery.

15. The apparatus of claim 14, wherein said at least one filter is separate from said body.

16. The apparatus of claim 15, wherein said at least one filter is adapted to be worn over at least one eye of a user.

17. A hand-held dental health kit comprising:
an implement body having a proximal handle and a distal end;
a head interface at the distal end of the body, where the head interface is adapted to receive each of a plurality of detachable heads and transmit energy from a power source to an attached head;
a first detachable head comprising at least one light-emitting diode mounted on the head, which diode is effective when placed in a mouth to emit radiation having a peak intensity in the wavelength range of about 390 nm to about 450 nm that causes visually detectable differential yellow-green and red-orange fluorescence emissions from normal tooth surfaces and abnormal tooth surfaces, respectively; and
a filter external of said handle and positioned to filter said differential fluorescence emissions for direct visualization by the user, said filter being a cut-off filter that does not pass light having a wavelength below about 520 nm.

18. The kit of claim 17, wherein said light-emitting diode is effective to emit radiation having a peak intensity at a wavelength of about 405 nm.

19. The kit of claim 17, further comprising a second detachable head having a plurality of bristles adapted for cleaning teeth, wherein the second detachable head transmits energy from the head interface to the bristles.

20. The kit of claim 17, wherein the handle includes a switch to selectively energize and de-energize the head interface.

21. The kit of claim 20, wherein the switch further selects between two or more different spectra of radiation being produced by the first detachable head.

22. The kit of claim 17, wherein the head interface transmits energy in the form of mechanical motion.

23. The kit of claim 17, wherein the head interface transmits energy in the form of electrical energy.

24. A hand-held dental implement for detecting abnormal tooth surface conditions, comprising:
a handle having a proximal end and distal end;
a battery chamber in said handle, for receiving a battery;
a light emitting diode mounted on said device, said light emitting diode electrically connected to said battery chamber, said light emitting diode energizable by a battery received in said battery chamber;
said light emitting diode insertable into the mouth of a user and effective to emit a light having a peak intensity in the wavelength range of about 390 nm to about 450 nm to tooth surfaces sufficiently to cause visually detectable differential yellow-green and red-orange fluorescence emissions from normal tooth surfaces and abnormal tooth surfaces, respectively; and
a filter external of said handle and positioned to filter said fluorescence emissions for direct visualization by the user of fluorescence emissions in the green-yellow wavelength range and orange-red wavelength range.

25. An apparatus for examining tooth surfaces for abnormal surface conditions, comprising:
a light-emitting diode adapted when energized to emit light in a wavelength range from 390 to 450 nm, said light effective to cause visually detectable differential yellow-green and red-orange fluorescence emissions from normal tooth surfaces and abnormal tooth surfaces;
means for energizing said light-emitting diode;

at least one filter for filtering said fluorescence emissions to facilitate visualization of said fluorescence in the green-yellow wavelength range and orange-red wavelength range, wherein said visualization consists of at least one of:
  direct visualization by a user's eye, and
  indirect visualization by a user by way of contemporaneous imaging.

26. A hand-held dental health kit comprising:

an implement body having a proximal handle and a distal end;

a head interface at the distal end of the body, where the head interface is adapted to receive each of a plurality of detachable heads and transmit energy from the power source to an attached head;

a first detachable head comprising at least one light-emitting diode mounted on the head, which diode is effective when placed in a mouth to emit radiation having a peak intensity in the wavelength range of about 390 nm to about 450 nm that causes visually detectable differential yellow-green and red-orange fluorescence emissions from normal tooth surfaces and abnormal tooth surfaces, respectively; and a filter external of said handle and positioned to filter said differential fluorescence emissions for direct visualization by the user of fluorescence emissions in the green-yellow wavelength range and orange-red wavelength range.

* * * * *